(12) United States Patent
Wu et al.

(10) Patent No.: US 9,915,617 B2
(45) Date of Patent: Mar. 13, 2018

(54) PORTABLE ELECTRONIC ASSAY DEVICE

(71) Applicant: TAIDOC TECHNOLOGY CORPORATION, New Taipei (TW)

(72) Inventors: Chia-Chi Wu, New Taipei (TW); Tien-Jung Tsai, New Taipei (TW); Chih-Hao Chen, New Taipei (TW)

(73) Assignee: TAIDOC TECHNOLOGY CORPORATION, New Taipei (TW)

( * ) Notice: Subject to any disclaimer, the term of this patent is extended or adjusted under 35 U.S.C. 154(b) by 304 days.

(21) Appl. No.: 14/807,816

(22) Filed: Jul. 23, 2015

(65) Prior Publication Data
US 2016/0025640 A1    Jan. 28, 2016

(30) Foreign Application Priority Data
Jul. 28, 2014 (TW) .............................. 103125677 A

(51) Int. Cl.
| | |
|---|---|
| *G01N 21/78* | (2006.01) |
| *A61B 10/00* | (2006.01) |
| *A61B 5/1455* | (2006.01) |
| *G01N 21/77* | (2006.01) |

(52) U.S. Cl.
CPC ........... *G01N 21/78* (2013.01); *A61B 5/1455* (2013.01); *A61B 10/0012* (2013.01); *A61B 10/0045* (2013.01); *G01N 21/77* (2013.01); *A61B 2010/0006* (2013.01); *A61B 2562/0295* (2013.01); *G01N 2021/7759* (2013.01); *G01N 2021/7773* (2013.01); *G01N 2201/0221* (2013.01)

(58) Field of Classification Search
CPC ............ A61B 10/0012; A61B 10/0045; A61B 2010/0006; A61B 2562/0295; A61B 5/1455; G01N 2021/7759; G01N 2021/7773; G01N 21/77; G01N 21/78; G01N 2201/0221
See application file for complete search history.

(56) References Cited

U.S. PATENT DOCUMENTS

2013/0171028 A1* 7/2013 Shaffer .............. G01N 21/8483
422/82.09

* cited by examiner

*Primary Examiner* — Samuel P Siefke
(74) *Attorney, Agent, or Firm* — Chun-Ming Shih

(57) ABSTRACT

The present invention is related to a portable electronic assay device, a portable assay device and a kit thereof. The portable electronic assay device is used for determining a result of an assay performed using a test strip comprises a casing, an optical module, a light detector, and a processor. The casing comprises a transmissive part. The optical module emits a detecting light signal and display light signal. The detecting light signal is illuminated to the test strip and the display light signal is illuminated to the transmissive part. The light detector detects light from the test strip so as to obtain a detecting signal. The processor receives the detecting signal compared with a default value so as to obtain an assay result. The assay result is displayed on the transmissive part. Therefore, it provides simple structure of the assay device for displaying the assay result rapidly and correctly.

18 Claims, 9 Drawing Sheets

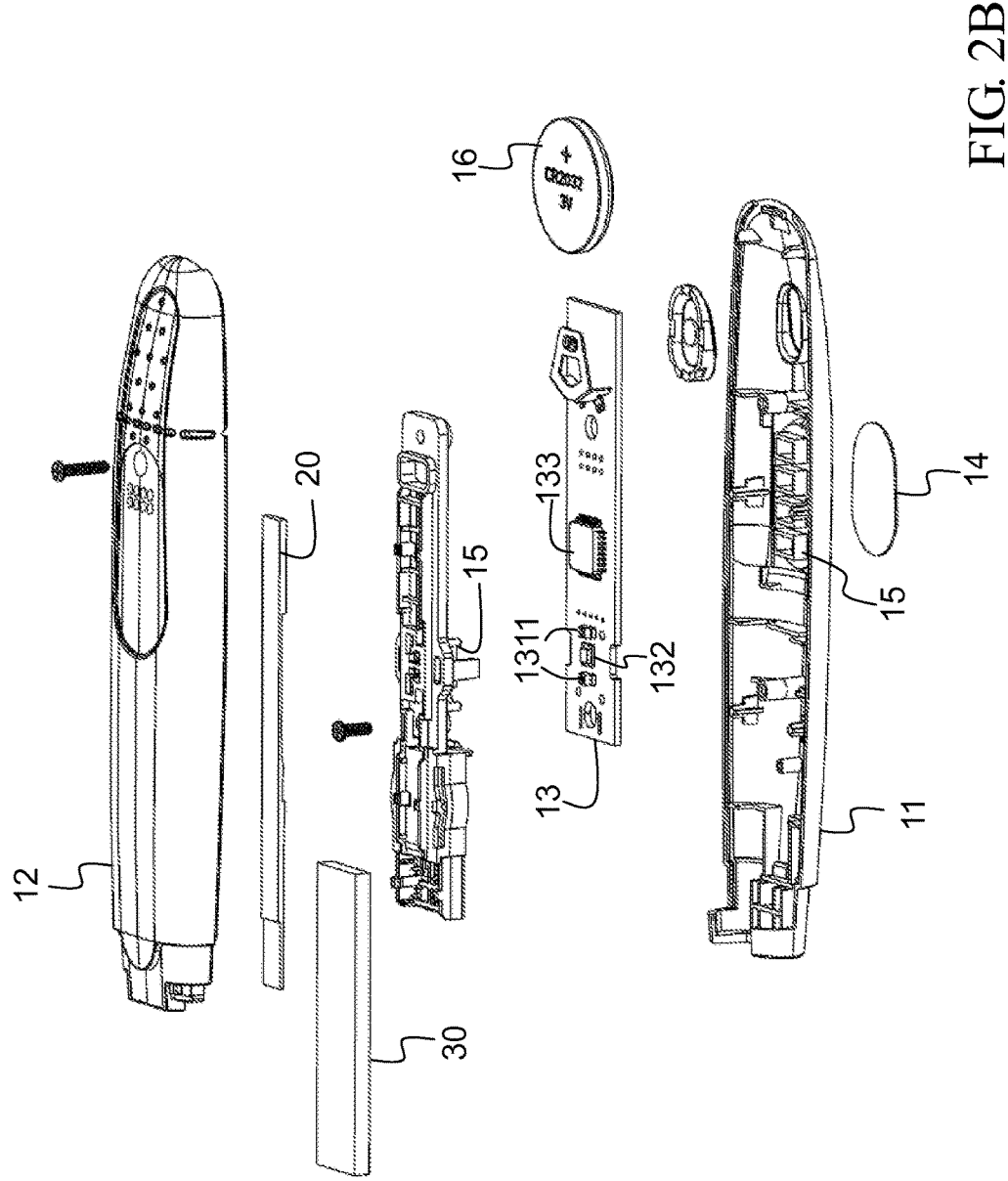

PORTABLE ELECTRONIC ASSAY DEVICE

BACKGROUND OF THE INVENTION

Field of the Invention

The invention relates to a portable electronic assay device, a portable assay device and a kit thereof, it particularly relates to a portable assay device and a kit thereof with simple structure to display a physical examination assay result rapidly.

Description of the Related Art

With the advance of medical device industry, the growing popularity of portable physiological signal or the medical examining device is not limited to use by medical professionals, but also convenient to the ordinary users who can measure by themselves at home.

Comparing to the large complex diagnostic instruments in the laboratories or in the medical institutions, the demands of the portable physiological examining device are lightweight and rapid diagnosis which is more conforming to the needs of the general public.

This kind of portable physical examining device usually goes with liquid crystal display (LCD) to present an assay result, but there is a certain complexity of manufacturing process of LCD module. It gets so time consuming during manufacturing, and also increases the difficulty of assembling while mounting LCD on the portable physical examining devices. Besides, the complex structure of LCD module will increase variance factors of damage, influence the display performance of assay results and the correctness of users read. Especially when the liquid crystal is broken, the users will not able to read the assay result, for this reason the entire device needs to be replaced. The risk of operating yield will influence the life time of portable physical examining device.

Thus, for how to provide a display device with simple structure and easy for users to read correctly within the lightweight portable physical examining device is what the manufacturers need to be further improved.

SUMMARY OF THE INVENTION

In order to improve the conventional deficiencies above, the present invention provides a portable electronic assay device to let users interpret assay results clearly with a simple structure of display design where inside the lightweight portable device which is limited by the volume.

The present invention provides a portable electronic assay device allowing users to read assay results easily with a simple structure of a transmissive design.

The present invention provides a portable electronic assay device, the manufacturing process of its display device is easy. It also raises the entire production efficiency, and reduces the manufacturing cost.

The present invention provides a portable electronic assay device with a simple structure of the display device. It reduces the probability of replacing the portable electronic assay device and also extends its life time which used to be broken and unable to read correctly due to a complex structure of the display device.

In order to achieve any one of the purpose above, the present invention provides a portable electronic assay device for determining an assay result of a test strip, the device comprising:

a casing comprising an opening and a containing space, the containing space used for containing the test strip;

a shading positioned at the opening of the casing, which comprises a transmissive part;

an optical module used for illuminating a detecting light signal and a display light signal, the detecting light signal is emitting to the test strip, and the display light signal is emitting to the shading;

a light detector used for detecting the light from the test strip to obtain a detecting signal; and a processor connected to the optical module and the light detector to receive the detecting signal and compare with a default value to obtain an assay result, and then illuminating the transmissive part by emitting the display light signal based on the assay result.

In an embodiment in accordance with the present invention, the optical module comprises a detecting light source and a display light source, the detecting light source emits the detecting light signal, and the display light source emits the display light signal.

In an embodiment in accordance with the present invention, the detecting light source comprises at least three detecting light sources, respectively used for illuminating light incident upon at least three spatially separated regions of the test strip alternately, wherein at least three regions are a test zone, a control zone and a reference zone.

In an embodiment in accordance with the present invention, the detecting light source comprises a first detecting light source and a second light source, the first detecting light source illuminates to a test zone on the test strip, and the second light source illuminates to a control zone on the test strip.

In an embodiment in accordance with the present invention, the display light source positioned at the corresponding place to the transmissive part.

In an embodiment in accordance with the present invention, the shading is a partially opaque background printing, and the transmissive part is an area without opaque background printing. In an embodiment in accordance with the present invention, the shading is Mylar.

In an embodiment in accordance with the present invention, the transmissive part comprises at least two transmissive patterns, and the transmissive patterns are different, and the display light source comprises at least two display light sources corresponding to the different transmissive patterns of the shading respectively, and the transmissive patterns used for corresponding to the assay result or a processing procedure.

In an embodiment in accordance with the present invention, the display light source comprises at least two display light sources, the color of the display light sources are different, and used for corresponding to the different assay results or a processing procedure.

In an embodiment in accordance with the present invention, an electronic assay device can further comprise a circuit board fixedly connected inside the casing, the optical module, the light detector, and the processor can be positioned on the circuit board.

In an embodiment in accordance with the present invention, an electronic assay device can further comprise a baffle used for covering an external light source or interferences between each light sources.

In an embodiment in accordance with the present invention, the material of the casing is opaque.

From another point of view, the present invention provides a portable electronic assay device for determining an assay result of a test strip, the test strip used for detecting at least a performance of an analyte in a specimen, the device comprising:

a casing used for providing a containing space;

a sensing module positioned in the containing space to detect the analyte on the test strip to obtain a sensing signal;

at least two light sources positioned in the containing space, starting up the different light sources based on the sensing signal;

a shading positioned at a side of the at least two light sources, comprising a transmissive part, the transmissive part respectively corresponds to different positions of the light source to display the assay result.

From another point of view, the present invention provides a portable electronic assay device used for detecting a performance of at least an analyte in a specimen, the device comprising:

a test strip comprising a single flow path, a test zone and a control zone, the test zone used for fixing a substance which can react with the analyte, and displaying the performance of the analyte;

a casing comprising an opening and provides a containing space, the containing space contains the test strip;

a shading positioned at an opening of the casing, comprising a transmissive part;

an optical module used for illuminating a detecting light signal and a display light signal, the detecting light signal used for illuminating to the test strip, the display light signal used for illuminating to the shading;

a light detector used for detecting the light on the test strip so as to obtain a detected signal; and a processor electrically connected to the optical module and the light detector to receive the detected signal, and compare with a default value to obtain an assay result, and emitting to the transmissive part of the shading by illuminating the display light signal base on the assay result.

From the other point of view, the present invention provides a pregnancy test kit comprising the portable electronic assay device and the single test strip or a plurality of test strips as described above.

From the other point of view, the present invention provides an ovulation test kit comprising the portable electronic assay device and a plurality of test strips as described above.

From the other point of view, the present invention provides a portable electronic assay device for determining an assay result of a test strip, the device comprising:

a casing comprising a transmissive part and providing a containing space, the containing space used for containing the test strip;

an optical module illuminating a detecting light signal and a display light signal, wherein the detecting light signal is illuminated to the test strip, and the display light signal is illuminated to the transmissive part;

a light detector detected the light from the test strip to obtain a detected signal; and a processor electrically connecting to the optical module and the light detector to receive the detected signal, and compare with a default value to obtain an assay result, and emitting to the transmissive part by illuminating the display light signal based on the assay result.

In an embodiment in accordance with the present invention, the display light signal comprises at least two display light signals, the color of the display light signals are different, used for corresponding to different assay results or different processing procedures.

In an embodiment in accordance with the present invention, the display light signal comprises different wavelengths of display light signals, different intensity of display light signals, different frequencies of display light signals or any combination of the above.

In an embodiment in accordance with the present invention, the different amounts of display light signal is corresponding to the different assay results and different processing procedures.

Based on the described above, the portable electronic assay device in accordance with the present invention is used for detecting an assay result of a physiological signal on a test strip. Emitting to the different transmissive part by illuminating the display light signal base on different assay results or processing procedures can complete the purpose of displaying. The display device is not only with a simple structure, but allowing users to read the assay results fast and correct easily.

In order to make the features and the advantages more realizable in the present invention, the following description and accompanying drawings are some examples in accordance with the present invention.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2B shows another side of the portable electronic assay device in FIG. 2A in an exploded perspective view;

DESCRIPTION OF THE PREFERRED EMBODIMENTS

Figure 1:
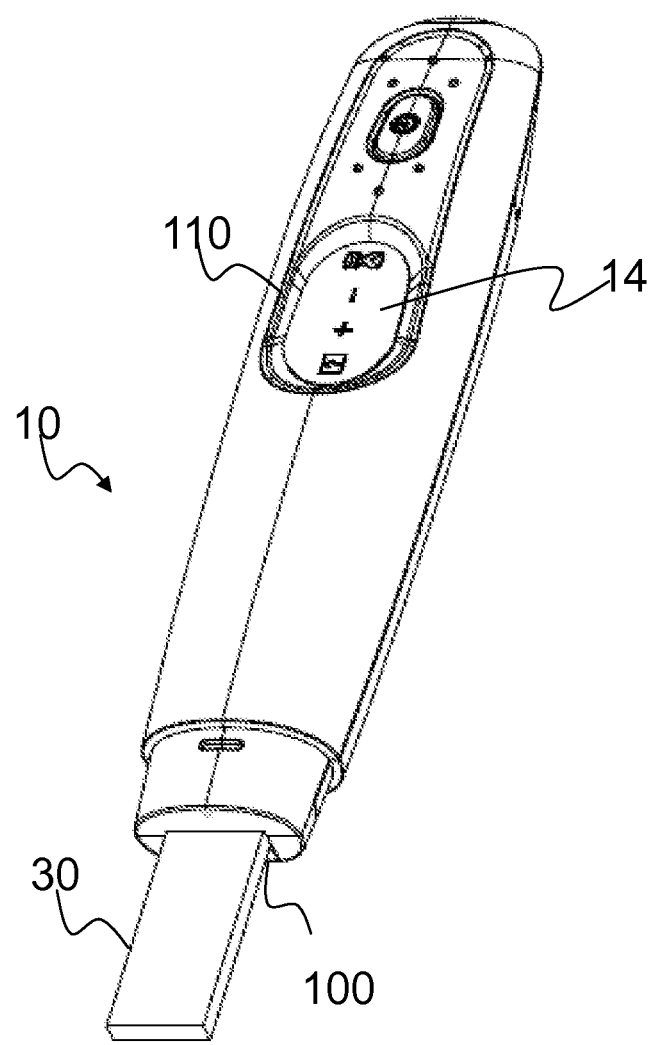
FIG. 1 shows a preferred embodiment of a portable electronic assay device according to the present invention in a schematic perspective view.

A conventional portable electronic assay device in the physiological signal examination field as described above usually uses LCD module as display device, and the LCD module is made with multiple mixed structures, which includes a light source, a reflecting plate, an optical film, a polarizer, a glass substrate, and a liquid crystal. The manufacturing process of the LCD module is complicated and time consuming, it's not only increasing the installation difficulty, decreasing the production efficiency, but also building up the production costs. Especially the complex structure of LCD module will increase the damage probability of partial structures, and causing the users read the assay results incorrectly.

On the contrary, an embodiment of a portable electronic assay device in accordance with the present invention controls a display light source in accordance with different assay results inside the portable electronic assay device and emits to a transmissive part, each transmissive part collocates with a display light source to show the different assay results, the users can interpret the assay result easily and rapidly by using a display device with a simple structure. The following detailed description and accompanying drawings are some examples in accordance with the present invention. The same symbol herein in the drawings indicates the same or similar structure.

Figure 2A:
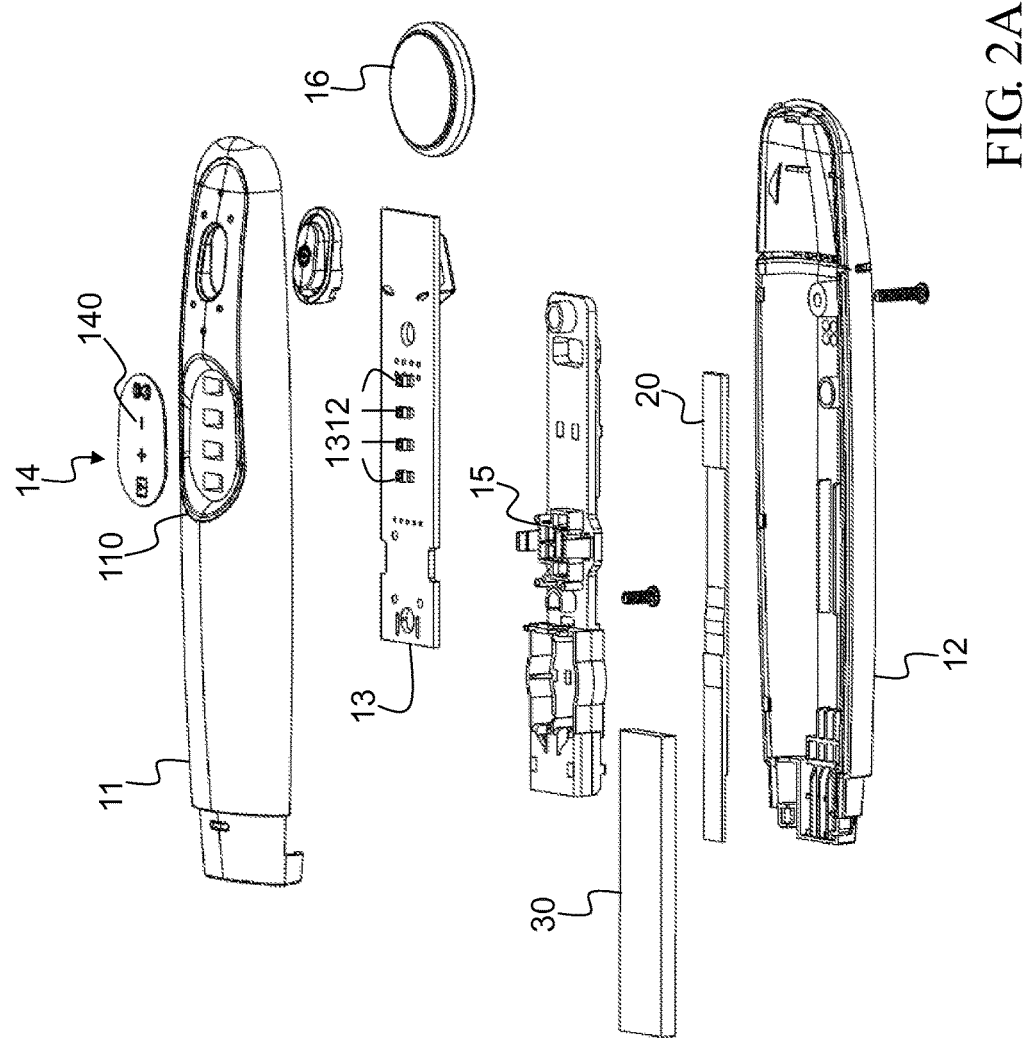
FIG. 2A shows a preferred embodiment of the portable electronic assay device in FIG. 1 in accordance with the present invention in an exploded perspective view.

FIG. 1 shows a preferred embodiment of a portable electronic assay device according to the present invention in a schematic perspective view. FIG. 2A shows a preferred embodiment of the portable electronic assay device in FIG. 1 in accordance with the present invention in an exploded perspective view. FIG. 2B shows another side of the portable electronic assay device according to FIG. 2A in an exploded perspective view. Please refer to FIGS. 1 and 2B in combination. In accordance with the present embodiment, a portable assay device comprises a portable electronic assay device and a test strip (20), the test strip (20) is used for examining at least a performance of an analyte in a specimen, the portable electronic assay device is used for detecting an assay result of the test strip. Preferably, the test strip is a single test strip, but the present invention shall not be limited in this. Preferably, the specimen is in a liquid phase, and more preferably, the specimen is a liquid sample obtained from human body, for example, blood, urine, plasma, serum, Cerebro-spinal fluid, spinal fluid or other body fluids. Preferably, the analyte can be hormone, and more preferably, the analyte can be human chorionic gonadotropin (hCG) or luteinizing hormone (LH). Preferably, the portable assay device can be a pregnancy test kit or an ovulation test kit, and it comprises the portable electronic assay device and a plurality of test strips, but the present invention shall not be limited in this.

The portable electronic assay device comprises a casing (10), a circuit board (13) and a shading (14), and preferably, the portable electronic assay device further comprises a baffle and a power source.

The casing is preferably made by opaque and impermeable materials, and even if there is an ambient light piercing through, it would be a very small amount. The casing (10) comprises a top cover (11) and a bottom cover (12), and combines the top cover (11) and the bottom cover (12) to form an inlet port (100) and a containing space. The inlet port (100) is used for providing the specimen to access to the portable electronic assay device.

Preferably, the portable electronic assay device further comprises a specimen receiving unit (30) and disposed at the inlet port (100). One side of the specimen receiving unit (30) protrudes from the inlet port (100) and uses for receiving the specimen, and the other side of receiving unit (30) overlaps with the test strip (20) to deliver the specimen to the test strip, but the present invention shall not be limited in this.

The casing (10) can comprise an opening (110), the opening is used for providing users a display interface to read the assay result. More specifically, the shading (14) is positioned at the opening (110) to display different assay results. Preferably, the opening (110) is positioned at the top cover (11), but the invention shall not be limited in this.

The containing space is used for containing the test strip (20) and the circuit board (13). The circuit board (13) is connected inside the casing (10), and it comprises an optical module (131), a light detector (132) and a processor (133). Preferably, the optical module (131), the light detector (132) and the processor (133) are positioned on the circuit board (13). The optical module (131) preferably comprises a detecting light source (1311) and a display light source (1312). In a preferred embodiment of the present invention, the detecting light source (1311) and the display light source (1312) are positioned at the different sides of the circuit board (13) respectively (as shown in FIG. 2A and FIG. 2B), but the present invention shall not be limited in this. Those skilled in the art can change the permutation and combination of the detecting light source (1311) and the display light source (1312) arrangement on the circuit board (13). The detecting light source (1311) is used for emitting detecting light to the test strip (20), and the display light source is used for emitting display light to the shading (14). The action principle of the optical module (131), the light detector (132) and the processor (133) will be described in detail later.

Figure 3:
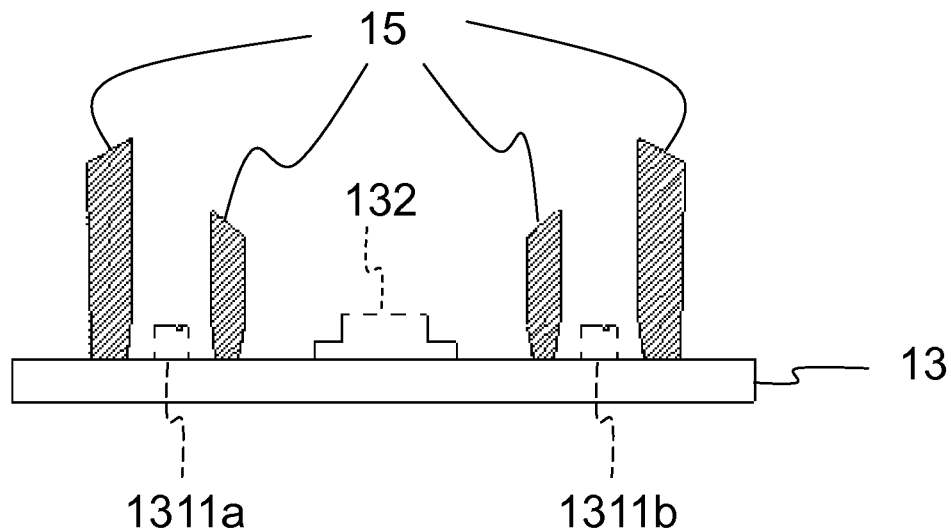
FIG. 3 shows a portable electronic assay device in FIG. 1 in accordance with the present invention in a partial inner structural schematic view.

FIG. 3 shows a portable electronic assay device in FIG. 1 in accordance with the present invention in a partial inner structural schematic view. Please refer to FIGS. 2A and 3 in combination. In a preferred embodiment of the present invention, the portable electronic assay device further comprises a baffle (15). The baffle (15) is used for covering an external light source or the interferences between each light sources. Preferably, the baffle (15) comprises a plurality of covers and openings, the covers are positioned between each light sources and the light detector (132), the opening corresponds to those light sources respectively. For example, the baffle (15) can located respectively corresponding to the detecting light source (1311) and the display light source (1312) in order to enhance the direction centralization of divergent light. More preferably, the baffle (15) can be connected with the casing (10). The portable electronic assay device further comprises a power source (16) for providing the power, preferably, the power source (16) can be a button cell battery.

Figure 4:
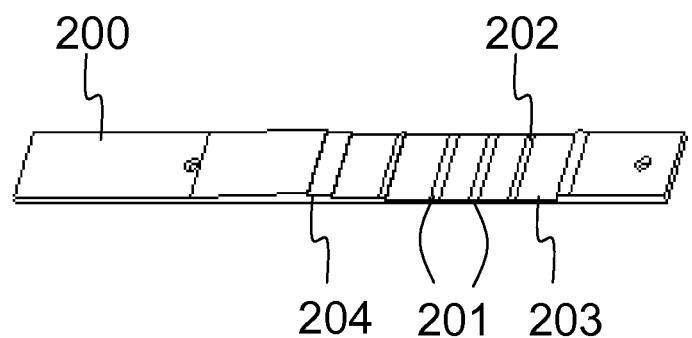
FIG. 4 shows a preferred embodiment of a test strip in accordance with the present invention in a schematic perspective view.

FIG. 4 shows a preferred embodiment of a test strip in accordance with the present invention in a schematic perspective view. Please refer to FIGS. 2A, 2B and 4 in combination. In a preferred embodiment of the present invention, the test strip (20) is used for detecting the analyte with the portable electronic assay device. The detection kinds can be pregnancy test, ovulation test, urine test, and drug test etc. The test strip (20) can be a single flow path comprises a test zone (201) and a control zone (202), and there is a distance between the test zone (201) and the control zone (202).

Preferably, the test strip (20) can further comprise a specimen pad (200) and a reference zone (203). The specimen pad (200) is used for receiving the specimen, preferably, the specimen pad (200) can deliver the specimen by contacting with the specimen receiving unit. A substance is immobilized to react with the analyte and displaying the performance of the analyte at the test zone (201). The control zone (202) is used for determining that whether the test strip can be used normally or not. Preferably, the control zone (202) is positioned at the downstream from the specimen receiving region on the test strip (20), the reference zone (203) is used for providing the detecting background value of the test strip (20). Preferably, the test strip (20) can comprise a plurality of test zones (201), but there is a distance between each test zone. The plurality of test zones (201) can detect different kinds of analyte or different concentrations but the same kind of the analyte.

For example, the analyte can be hCG, the test zone (201) can comprise a goat anti-α hCG, and the control zone (202) can comprise a goat anti-mouse IgG antibody, preferably, the antibodies described above are immobility. The test strip can further comprise a conjugated pad (204) positioned at the upstream of the test zone (201) and the control zone (202), and the conjugated pad (204) comprises a mobilized antibody. Preferably, the mobilized antibody is a mouse anti-βhCG antibody conjugated with colloid gold. Assuming that the specimen presents in hCG, then it will be revealed when passing through the test zone (201) by an antigen and antibody binding reaction. No matter there is hCG presented in the specimen or not, when the specimen passing through the control zone (202), it will be determined whether the current test is succeeded by combining the mobilized antibody at the upstream of the conjugated pad (204) and the goat anti-mouse IgG antibody at the control zone (202).

Figure 5:
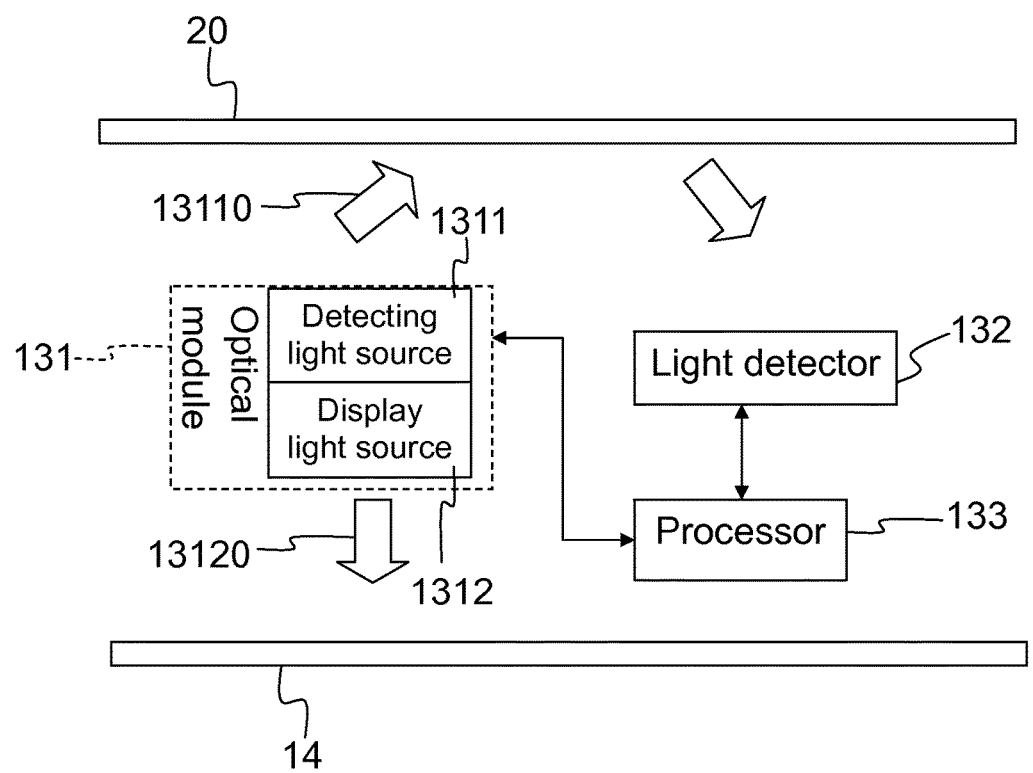
FIG. 5 shows a first preferred embodiment of a portable electronic assay device in accordance with the present invention in a functional block diagram.

FIG. 5 shows a first preferred embodiment of a portable electronic assay device in accordance with the present invention in a functional block diagram. Please refer to FIGS. 2A to 5 in combination. In a preferred embodiment of the present invention, the optical module (131) is used for emitting a detecting light signal (13110) and a display light signal (13120), and preferably, the detecting light source (1311) is used for emitting the detecting light signal (13110) to illuminate the test strip (20) and the display light source (1312) is used for emitting the display light signal (13120) to illuminate the shading (14). Preferably, the optical module (131) can be light-emitting diode (LED), and more preferably, the detecting light signal (13110) can be green light, blue light and yellow green light, but the invention shall not be limited in this. Those skilled in the art can change the kind and the amount of the detecting light source or the display light source. The following further descriptions are about the amount of the detecting light sources and the zones of the test strip.

The detecting light source (1311) can comprise a first detecting light source (1311a) and a second detecting light source (1311b) (as shown in FIG. 2B and FIG. 3). Preferably, the first detecting light source (1311a) and the second detecting light source (1311b) emit light to the test zone (201) and the control zone (202) of the test strip (20) respectively or the first detecting light source (1311a) and the second detecting light source (1311b) emit light to the test zone (201) and the reference zone (203) of the test strip (20) respectively, but the invention shall not be limited in this.

In another example, the detecting light source (131) can comprise at least three detecting light sources respectively illuminating light incident upon at least three spatially separated regions of the test strip alternately. Preferably, the at least three regions are a test zone (201), a control zone (202) and a reference zone (203). In accordance with the other embodiments, the at least three regions can be a plurality of test zones and the control zone, but the invention shall not be limited in this.

While the detecting light source (1311) is emitting the detect light signal (13110) to illuminate the different zones of the test strip (20), the light detector (132) detects the light from the test strip (20) to obtain a detecting signal. Preferably, the light detector (132) can be a photodiode. In a preferred embodiment of the present invention, it takes the light detector (132) detecting a reflected light as an example, but the invention shall not be limited in this. The light detector (132) can also be used for detecting a transmissive light. The reflected light means that the light emits from the detecting light source (1311) to illuminate the test strip and reflects to the light detector (132) from the test strip (20), in which the light detector (132) and the detecting light source (1311) are positioned at the same side. The transmissive light means that the light penetrates the test strip (20) and detected by the light detector (132), in which the light detector (132) and the light source (1311) are positioned at different sides. In order to achieve the purpose of receiving the reflected light, the test strip (20) usually uses a layer of reflective white material, therefore even if there is some light will penetrate a part of test strip, it still can be reflected by the reflective material.

The processor (133) electrically connects to the light detector, and more specifically, the processor (133) controls the luminous frequency and intensity of the optical module (131). On the other hand, when the light detector (132) generates the detecting signal delivering to the processor (133), the processor (133) receives the detecting signal and compares to a default value to obtain an assay result. For example, comparing the detecting signal from illuminating the test zone and the control zone on the test strip to that from the reference zone respectively can obtain a first result value and a second result value. Take the second result value to compare to a default value, and it will show that the test strip works properly if the second result value is exceeding the default control value, and it will indicate that the test strip may be a problem if the second result value is lower than the default control value, and it will also inform the users by displaying an error message. Comparing the first result value to a default result value, it will express as a positive result if the first result value exceeds the default result value, and it will express as a negative result if it lower than the default result value, but the invention shall not be limited in this.

The processor controls the display light source (1312) by emitting the display light signal (13120) based on the assay result to illuminate the shading (14). Preferably, the display light source (1312) can be a single color light source or multicolor light sources. The shading (14) comprises a transmissive part (140) and is constituted by an opaque background printing, and the transmissive part (140) is formed by an area without opaque background printing, but the invention shall not be limited in this. Preferably, the shading (14) is Mylar, and the transmissive part (140) can use numbers, characters, symbols or patterns to display the assay result. The display light source (1312) displays the different assay results through the shading (14) which the operating principle will be described later.

Figure 6:
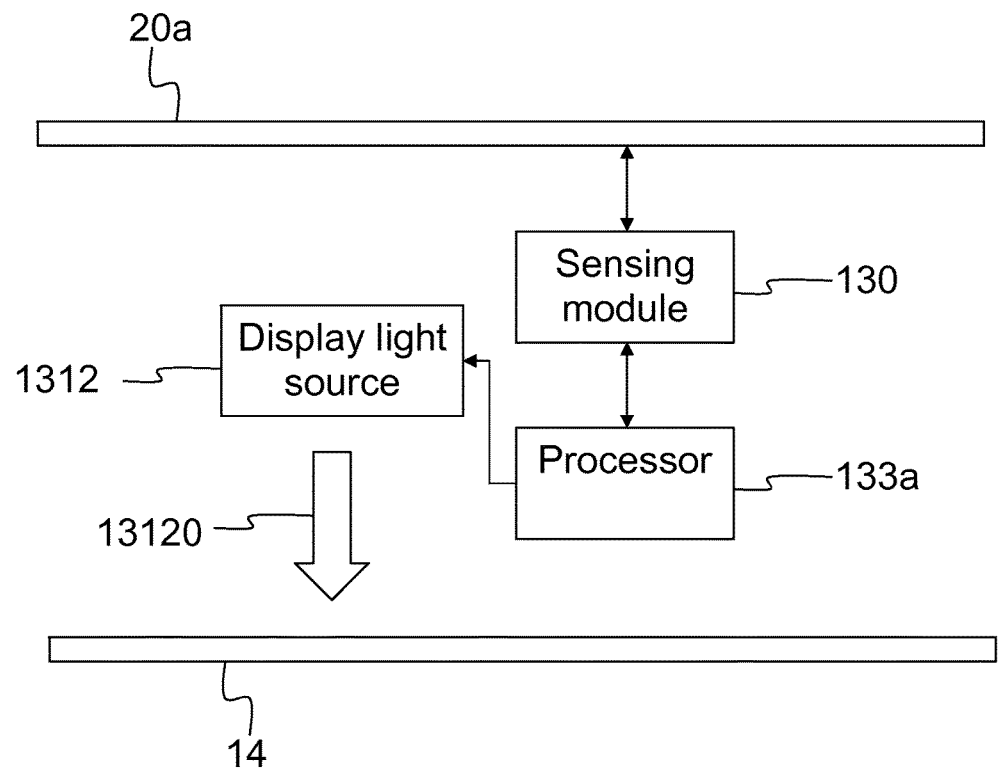
FIG. 6 shows a second preferred embodiment of a portable electronic assay device in accordance with the present invention in a functional block diagram.

FIG. 6 shows a second preferred embodiment of a portable electronic assay device in accordance with the present invention in a functional block diagram. The portable assay device in FIG. 6 is similar to the portable assay device in FIG. 5, and the difference between them is the portable assay device in the second preferred embodiment comprising a sensing module (130), the sensing module (130) is being substituted for the optical module (131) and the light detector (132) in the first preferred embodiment. In a preferred embodiment of the present invention, the sensing module (130) detects the analytes on the test strip (20a) to obtain a sensing signal. For example, the test strip (20a) can be electrochemical sensing test strip, the sensing module (130) can be electrical sensing unit to detect an electrical signal changing occurring by electrochemical reacting between the test strip and the specimen, but the invention shall not be limited in this. The sensing module (130) electrically connects to the processor (133a), the processor (133a) receives the sensing signal and compares to a default value to obtain an assay result, and then controls the display light source (1312) according to the assay result to illuminate at the shading (14).

Figure 7A:
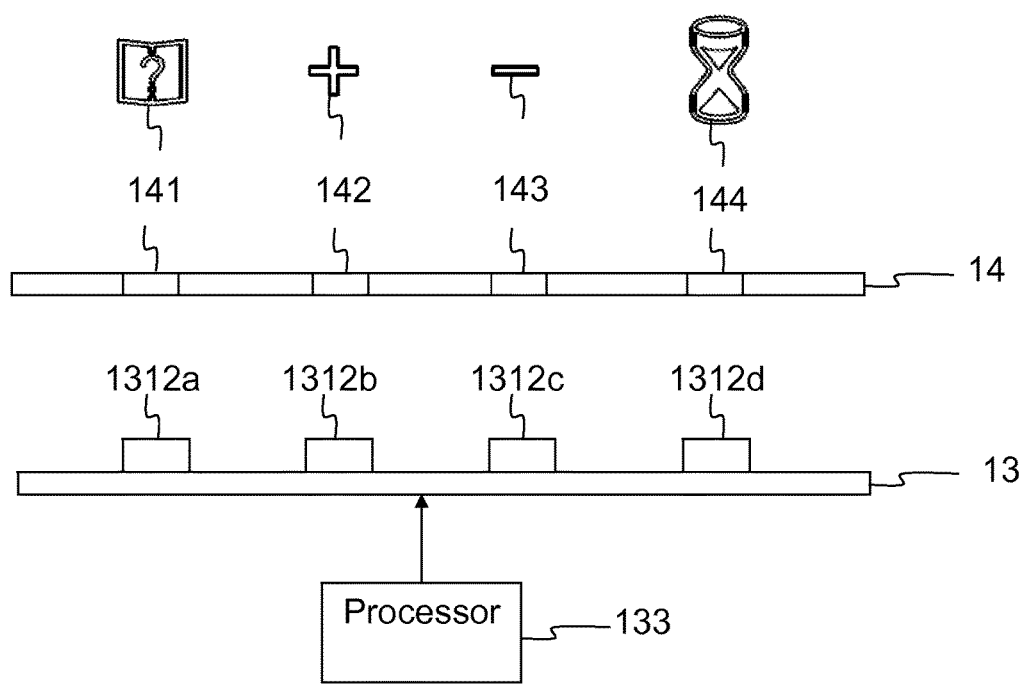
FIGS. 7A to 7C show the reading assay result of a portable electronic assay device in FIG. 1 in accordance with the present invention in a partial structural schematic view.
Figure 7B:
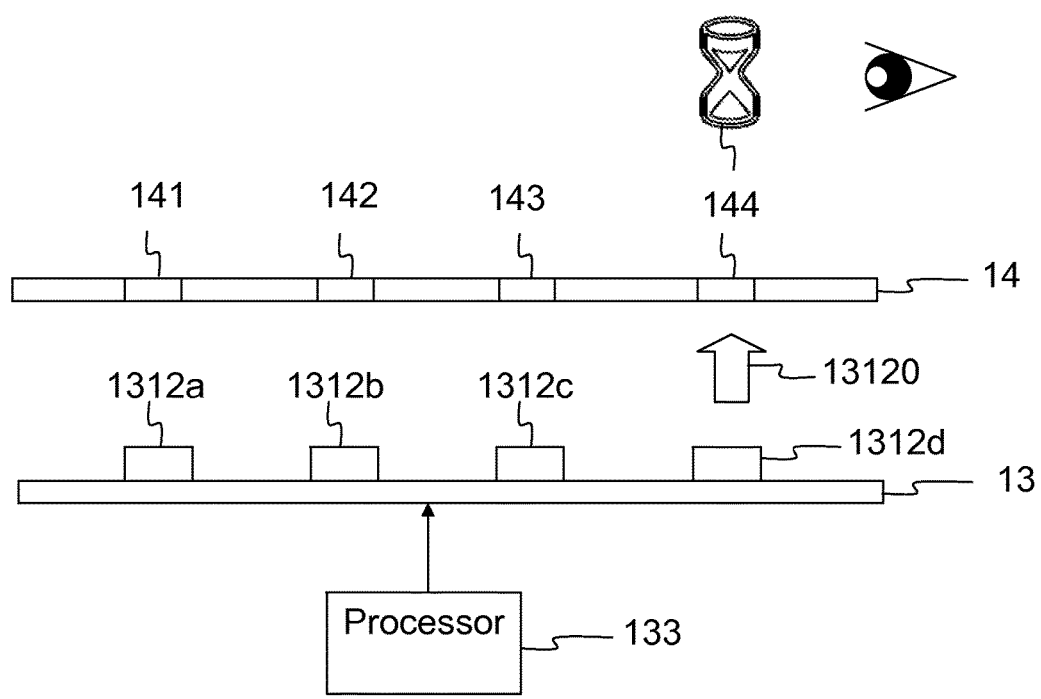
Figure 7C:
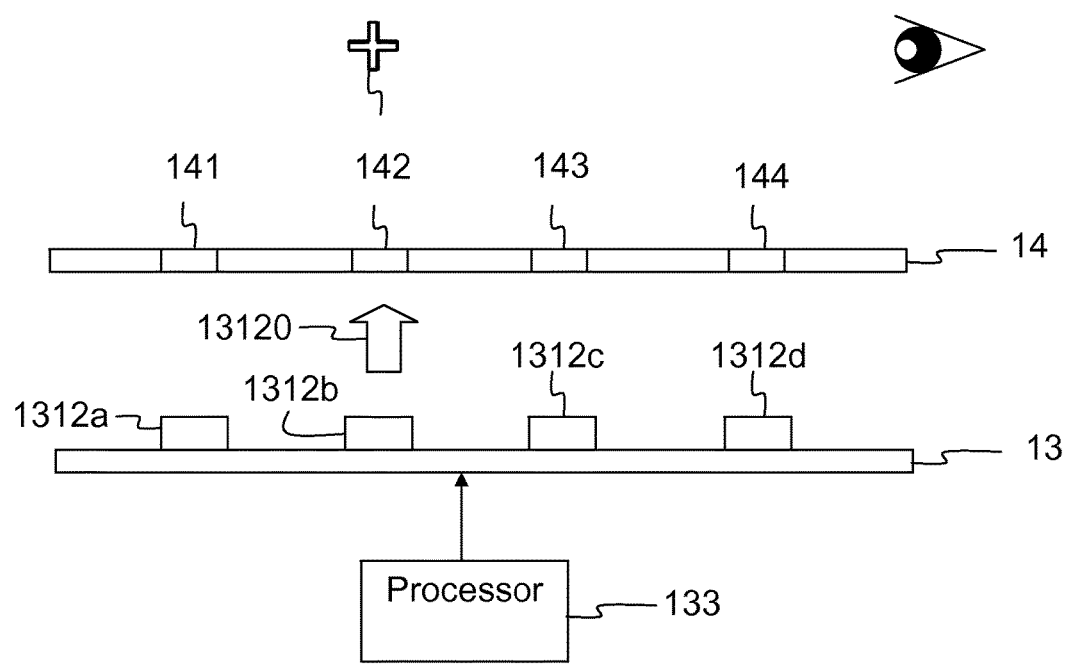

FIGS. 7A to 7C show the reading assay result of a portable electronic assay device in FIG. 1 in accordance with the present invention in a partial structural schematic view. Please refer to FIGS. 2A, 4 and 7C in combination. In a preferred embodiment of the present invention, the transmissive part (140) is taking the transmissive pattern as an example, but the invention shall not be limited to this. The display light source (1312) is positioned corresponding to the transmissive part (140). More specifically, the display light source (1312) comprises at least two display light sources, and each display light source is positioned on the circuit board (13) respectively corresponding to the different transmissive part (140) of the shading (14).

In a preferred embodiment of the present invention, the display light source (1312) is in a linear array corresponding to the transmissive part (140), but the invention shall not be limited in this. In accordance with the other embodiments, the display light source (1312) can be a matrix array corresponding to the transmissive part (140). Those skilled in the art can change the amount of the display light source (1312) and the arrangement corresponding to the transmissive part (140).

In a preferred embodiment of the present invention, the display light source (1312) comprises a first display light source (1312a), a second display light source (1312b), a third display light source (1312c) and a fourth display light source (1312d), the shading (14) comprises a first transmissive pattern (141), a second transmissive pattern (142), a third transmissive pattern (143) and a fourth transmissive pattern (144). The position of the first display light source (1312a) to the fourth display light source (1312d) on the circuit board (13) are corresponding to the position of the first transmissive pattern (141) to the fourth transmissive pattern (144) on the shading (14) respectively. The transmissive pattern is designed corresponding to the different assay results or a processing procedure. In a preferred embodiment of the present invention, the first transmissive pattern (141) uses a question mark to represent an error message, the second transmissive pattern (142) uses "+" to represent a positive result, the third transmissive pattern (143) uses "−" to represent a negative result, the fourth transmissive pattern (144) uses a funnel pattern to represent an assay analyzing processing procedure, but the invention shall not be limited in this, those skilled in the art can change the set pattern of the transmissive pattern and its correspondences as needed.

Considering a pregnancy test as an example, the second transmissive pattern can use smiling face pattern, baby face pattern, positive character or pregnant character to substitute for the "+" pattern to represent the positive result. The third transmissive pattern can use crying face pattern, prohibition sign, negative character or not pregnant character to substitute for the "−" pattern to represent the negative result, but the invention shall not be limited in this.

When the processor (133) compares the receiving detecting signal to the default value, the fourth display light source (1312d) is used for emitting the displaying light signal (13120) to the fourth transmissive pattern (144) (as shown in FIG. 7B). Due to the shading (14) is made by an opaque background printing, the rest of the transmissive patterns are not illuminated by the corresponding display light source respectively, thus it doesn't display the transmissive pattern, so the users could see the fourth transmissive pattern (144) illuminate through the opening (110) of the casing (10) to interpret the assay result and analyze the process which is in progress.

Similarly, if the comparison assay result of the processor (133) is positive, the second display light signal (1312b) is used for emitting the display light signal (13120) to the second transmissive pattern (142) (as shown in FIG. 7C), and the rest of the transmissive patterns are not illuminated by the corresponding display light source respectively, thus it doesn't display the transmissive pattern, so the users could see the second transmissive pattern (142) illuminate through the opening (110) of the casing (10) to interpret the assay result is pregnant.

Although the possible kinds of the portable electronic assay device, portable assay device and the kits in accordance with the present invention has been described in the embodiments above, those skilled in the art shall recognized that the portable electronic assay device, portable assay device and the kits can be designed differently. Therefore, the spirit of the present invention shall not be limited to these possible kinds of portable assay device in accordance with the present invention. In other words, used the portable electronic assay devices to detect the analytes in the specimen and to achieve the purpose of displaying the assay results by emitting the transmissive part with the display light source is the key spirit and scope of the present invention. The followings are some other embodiments in accordance with the present invention for those skilled in the art to know more about the spirit of the present invention.

According to the embodiment of the present invention in FIGS. 1 to 2B, the portable electronic assay device can further comprise a specimen receiving unit (30) is disposed at the inlet port (100), one side of the specimen receiving unit (30) protrudes from the inlet port (100) for receiving the specimen, and the other side of the specimen receiving unit (30) overlaps with the test strip (20) to deliver the specimen to the test strip which is only an alternative embodiment of the present invention. Those skilled in the art can change the way the specimen gets into the portable electronic assay device as needed. In accordance with the other embodiments, the specimen receiving unit can be integrated with the test strip into an individual test strip kit for the detection by inserting it into the portable electronic assay device from the inlet port. In another example, the specimen receiving unit can simultaneously overlap with a plurality of the test strip for delivering the specimen to detect different types or different concentrations of the analyte. In the other example, the specimen can be contacted with the test strip directly, the test strip is inserted into the portable electronic assay device directly from the inlet port, or the specimen can be contained in a reaction vessel for the detection by inserting it into the portable electronic assay device from the inlet port.

According to the embodiment of the present invention in FIGS. 2A, 7A to 7C, the shading (14) is constituted by the opaque background printing, the transmissive part (140) is formed by an area without opaque background printing which is only an alternative embodiment of the present invention. Those skilled in the art can change the manufacturing process and the materials of the transmissive and the opaque area as needed.

According to the embodiment of the present invention in FIGS. 1 to 2B, 5 and 6, the processor controls the display light source (1312) based on the assay result, illuminates the shading (14) by emitting the display light signal (13120). Preferably, the display light source (1312) can be a single color light source or multicolor light source, and display the assay result with different transmissive parts of the shading

(14) which is only an alternative embodiment of the present invention. In accordance with the other embodiments, it can identify different assay results by the color of different display light sources. For example, it represents the positive result when the display light source emits a red display light signal, and it represents the negative result when the display light source emits a green display light signal. Those skilled in the art can change the colors, amounts, or the types of the display light source, and its corresponding assay result and processing procedure.

Following the description above, it lets users identify different assay results by the color of different display light sources which is only an alternative embodiment of the present invention. In accordance with the other embodiments, through the combinations of the different display light source, the intensity or the frequency of the display light signal can be corresponded to the different assay results or different processing procedures. For example, it represents as the positive result when the luminous intensity of the display light signal get to 100% or the emitting frequency is 5 Hz, and it represents as the negative result when the luminous intensity of the display light signal get to 10% or the emitting frequency is 0.5 Hz, but the present invention shall not be limited in this.

In another example, here are a plurality of the display light sources, take FIG. 7A as an example, there are four display light sources. When the first display light source (1312a) to the fourth display light source (1312d) all emitting the display light signals is representing a first assay result, when the first display light source (1312a) to the third display light source (1312c) all emitting the display light signals is representing a second assay result, when the first display light source (1312a) and the second display light source (1312b) both emitting the display light signals is representing a third assay result, when the first display light source (1312a) emits the display light signal alone is representing to a fourth assay result, or if the first display light source (1312a) to the fourth display light source (1312d) emitting the display signals alternately in circles is representing to a processing procedure. Those skilled in the art can change different amounts of the display light source to emit different permutations or combinations of the display light signals to represent different assay results or the processing procedures as needed.

Following the description above, the display light signal illuminates at the shading (14), and display the assay result through the different transmissive part of the shading (14) which is only an alternative embodiment of the present invention. In accordance with the other embodiments, the transmissive part (140) can be formed on the casing (10), and the partial structure of the casing (10) is being substituted for the shading (14), the display light source illuminates at the transmissive part of the casing (10) to correspond to different assay results. For example, preferably, the partial structure of the casing (10) is a baffle (15), the transmissive part is an opening corresponding to the display light source, furthermore, the transmissive part is corresponding to a single display light source or a plurality of display light sources, more preferably, there are a plurality of openings at the baffle corresponding to the plurality of display light sources respectively, but the invention shall not be limited in this. It can also be sculptured or printed different characters or patterns at the position of the casing surface corresponding to the display light source to correspond to different assay results and different process procedures. Those skilled in the art can change the position of the transmissive part in the portable electronic assay device as needed.

According to the embodiment of the present invention in FIGS. 4 and 7A to 7C takes a pregnancy test as an example, which is only an alternative embodiment of the present invention. Those skilled in the art can change types of the analyte. In accordance with the other embodiments take a drug test as examples, the test strip can examine multiple items, the item that the test zone examined can be chose from Cocaine (COC), Tetrahydrocannibinol (THC), Methamphetamine (MET), Amphetamine (AMP), Ecstasy (MDMA), Morphine (OPI), Phencyclidine (PCP), Benzodiazepines (BZO), Barbiturates (BAR), Methadone (MTD), Tri-cyclic Antidepressants (TCA), Oxycodone (OXY), and any kinds of the combination above. Excepting MET and AMP cannot examine on the same test strip because it will interfere with each other due to the similar structural composition.

Accordingly, the present invention is corresponding to a portable electronic assay device, a portable assay device and a kit, detecting the analyte in a specimen in a lightweight portable electronic assay device, controlling the display light source to emit to the transmissive part by using different assay results, enhancing the convenience to the interpretation of the assay results by the users. Furthermore, there are also other advantages in some embodiments of the present invention exemplarily listed as follows:

1. The portable electronic assay device in accordance with the present invention using a light source and its corresponding transmissive design to provide a simple display structure to simplify the assembly process of an electronic assay device, raise the entire production efficiency, and reduce the manufacturing cost.

2. The portable electronic assay device in accordance with the present invention controls different light sources to emit to the corresponding transmissive parts through different assay results. Then the users can interpret the assay results via the corresponding transmissive patterns or collocate different aspects of displaying light source.

3. The portable electronic assay device in accordance with the present invention using different light sources to correspond to a transmissive part to display the detecting assay results, replace the complex display structure of liquid crystal module, reduce the damage probability of partial structures, and the risk of causing the users interpret the assay results incorrectly, extend the life time of the portable electronic assay device.

Although the present invention has been disclosed the embodiments as above, it should be understood those are given by way of illustration only, those skilled in the art will recognize that the present invention can be practiced with modification within the spirit and scope of the claims.

What is claimed is:

1. A portable electronic assay device for determining an assay result of an assay performed on a test strip, the device comprising:
   a casing core comprising an opening and a containing space for containing the test strip;
   a shading positioned at the opening and having a transparent figuration, wherein the shading is a single lamina;
   an optical module comprising a detecting light source for illuminating a detecting light to the test strip, and a display light source for illuminating, a display light to the transparent figuration;

a light detector for detecting the detecting light from the test strip to obtain a detected signal; and a processor electrically connected to the optical module and the light detector, and programmed to receive the detected signal and to compare the detected signal with a default value to obtain an assay result, and illuminating the display light directly passed through the transparent figuration of the shading for displaying the assay result.

2. The device as claimed in claim 1, wherein the detecting light source comprises at least three detecting light sources configured to, respectively illuminate light incident upon at least three spatially separated zones of the test strip alternately, wherein the at least three zones are a test zone, a control zone and a reference zone.

3. The device as claimed in claim 1, wherein the detecting light source comprises a first detecting light source and a second detecting light source, and the first detecting light source is for illuminating the detecting light to a test zone on the test strip and the second detecting light source is for illuminating the detecting light to a control zone on the test strip.

4. The device as claimed in claim 1, wherein the display light source positioned at a place where corresponds to a position of the transparent figuration.

5. The device as claimed in claim 4, wherein the display light source comprises at Fast two display light sources configured to respectively illuminate different kinds of color, wavelength, intensity, frequency, or any combination of above of the display light to indicate the different assay results or a processing procedure.

6. The device as claimed in claim 4, wherein the display light source comprises a plurality of display light sources configured to indicate the different assay result and/or a processing procedure by illuminating different numbers of the display light.

7. The device as claimed in claim 1, wherein the shading is printed an opaque background, and the transparent figuration is where the shading unprinted the opaque background area.

8. The device as claimed in claim 7, wherein the shading is Mylar.

9. The device as claimed in claim 7, wherein the transparent figuration is a Predetermined unchangeable transparent figuration.

10. The device as claimed in claim 7, wherein the transparent figuration comprises at least two different transparent figurations for indicating the different assay result or a processing procedure, and the display light source comprises at least two display light sources configured to respectively illuminate one to the transparent figuration of the shading at a time.

11. The device as claimed in claim 10, wherein the at least two different transparent figurations are configured to indicate a positive result and a negative result.

12. The device as claimed in claim 1, therein the material of the casing is opaque.

13. A portable electronic assay device for determining an assay result of a test strip, the test, strip used for detecting at least a performance of an analyte in a specimen, the device comprising:

a casing comprising a containing space;

a sensing module positioned in the containing space to detect the analyte on the test strip to obtain a sensing signal;

at least two light sources positioned in the containing space, for starting up the different light sources illuminating a display light based on the sensing signal;

a shading lamina positioned at a side of the at least two light sources, comprising at least two transparent figurations, wherein position of the two transparent figurations is respectively corresponds to position of the two light sources and the display light is directly passed through the transparent figuration of the shading for displaying the assay result.

14. The device as claimed in claim 13, wherein the material of the casing is opaque.

15. The device as claimed in claim 13, wherein the display light source comprises at least two display light sources configured to respectively illuminate different kinds of color, wavelength, intensity, frequency, or any combination of above of the display light to indicate the different assay results or a processing procedure.

16. The device as claimed in claim 13, wherein the display light source comprises a plurality of display light sources configured to indicate the different assay result and/or a processing procedure by illuminating different numbers of the display light.

17. The device as claimed in claim 13, wherein the shading is printed an opaque background, and the transparent figuration is where the shading unprinted the opaque background area.

18. The device as claimed in claim 17, wherein the transparent figuration is a predetermined unchangeable transparent figuration.

* * * * *